United States Patent [19]

Herlitze et al.

[11] Patent Number: 5,108,380
[45] Date of Patent: Apr. 28, 1992

[54] HUB MEMBER

[75] Inventors: Gerd Herlitze, Baunatal; Klaus-Joachim Schmidt, Ahnatal; Egon Lesemann, Melsungen; Hans-Otto Maier, Lohfelden; Karl-Friedrich Voges, Melsungen; Heinz G. Wiegel, Alheim-Heinebach, all of Fed. Rep. of Germany

[73] Assignee: B. Braun Melsungen AG, Melsungen, Fed. Rep. of Germany

[21] Appl. No.: 637,474

[22] Filed: Jan. 4, 1991

[30] Foreign Application Priority Data

Jan. 12, 1990 [DE] Fed. Rep. of Germany ....... 4000764

[51] Int. Cl.$^5$ .............................................. A61M 25/00
[52] U.S. Cl. ..................................... 604/283; 604/169
[58] Field of Search ............... 604/280, 283, 167, 168, 604/169, 200, 201, 213, 236, 237, 246, 247, 250, 256, 905; 128/912

[56] References Cited

U.S. PATENT DOCUMENTS

| 4,425,122 | 1/1984 | Cohen .................... 604/237 |
| 4,496,348 | 1/1985 | Genese et al. ............ 604/167 |
| 4,917,668 | 4/1990 | Haindl .................... 604/169 |
| 5,006,114 | 4/1991 | Rogers et al. ............ 604/169 |

FOREIGN PATENT DOCUMENTS 3809127 4/1989 Fed. Rep. of Germany ...... 604/283

Primary Examiner—C. Fred Rosenbaum
Assistant Examiner—Sharon Finkel
Attorney, Agent, or Firm—Spensley, Horn, Jubas & Lubitz

[57] ABSTRACT

A valve device for a hub member of a catheter or the like. An open cup-shaped hollow cylinder with a slit bottom portion is axially displaceable in the chamber of the housing of the hub member. In the closed position, a helical spring presses the edge of the opening of the hollow cylinder against the inner end of an insertion opening for a connecting member. The insertion opening is formed at the housing and has a diameter larger than the inner circumference of the edge of the opening of the hollow cylinder. The bottom portion is pulled into an adapted central hole of a closing ring fixed in the housing, through which hole the bottom portion may be pushed axially against the spring action for releasing its legs formed by the slit. Throughout this operation the resilient hollow cylinder is free of stresses, so that the edges of the slit in the bottom portion are not deformed. Nevertheless, the closing ring ensures an effective closure of the flow channel in the hub member, sealing it both against air entering the hub member and against blood oozing out.

6 Claims, 3 Drawing Sheets

FIG.4

HUB MEMBER

BACKGROUND OF THE INVENTION

1. Field of the Invention

The present invention relates to a hub member for a rigid or flexible medical conduit.

2. Description of Related Art

As used in the present application, the term "medical conduit" includes metal or plastic cannulas and flexible catheters or the like that are inserted for withdrawing blood or for supplying blood, infusion liquids or medicaments into the vessels of a patient. When the tip of the conduit enters the vessel, blood will flow back and will emerge from most of the known hub members. This should be prevented, due to the danger of the transmission of contagious diseases through the blood. Also, when replacing a continuing conduit by pulling the connecting member off the housing of the hub member, the same will be open and blood may flow therefrom. In a case in which the patient is unfavorably positioned, air may enter the venous system and cause air embolism.

In an attempt to remedy these deficiencies, a hub member with a valve device has been provided (German Patent 28 17 102). In this known device a disc of elastomeric material having a central slit therein is held in a radially extending groove in the wall of the chamber of the housing. Further, the housing contains an adjusting member in the form of a conical sleeve member which is advanced by the pressure of a connecting member; e.g. the hub of a steel cannula, insertable into an insertion opening of the housing, and which in this advanced position presses against the disc and penetrates the disc at least partly to open the slit.

In the case of this known device, the closure is of doubtful reliability after the steel cannula has been withdrawn, since it relies on the inherent resilience of the disc material which will deteriorate due to fatigue of the material. This is particularly so when the device is delivered as a ready for use set in which the smooth edges of the slit in the prestressed disc (which form lips) are deformed over a long time by a steel cannula. For this reason, it is possible that the deformed edges of the slit will not only refuse to sealingly close when the steel cannula is extracted, but they may even leave an open hole through which blood may ooze back.

In order to keep the size of this hole at a minimum, steel cannulas of a larger diameter have been provided in practice with a constriction arranged in the region of the elastomeric disc in the hub member. However, this constriction can only be provided with considerable production efforts. Moreover, the constriction forms a throttle point inside the cannula, so that tissue particles cut out when puncturing a tissue may get stuck at the throttle point and a successful puncture may not be indicated by outflowing blood. Therefore, the user may unnecessarily puncture the vessel several times, causing an inappropriate stress on the patient.

A further known puncturing and insertion device has a valve means with a resilient cup-shaped hollow cylinder, the bottom portion of which is slit (German Patent 31 47 609). In this known device an adjusting member axially displaceable in the chamber of the housing of the hub member and shaped as a jacket open at both ends serves to bias the bottom portion of the stationary cup-shaped hollow cylinder by radial pressure. Prior to use of the device, the inner end of the jacket only encloses the distal open end of the hollow cylinder so that its opposite bottom member is unstressed during storage time and no deformations will occur at the sealing lips that might lead to leakages. A connecting member (e.g. a cannula hub) is inserted in the outer end of the jacket facing the user. The connecting member, when being advanced axially for preparing the cannula tip for the puncture, pushes the inner jacket end entirely over the hollow cylinder and presses the bottom portion radially. In this position, the jacket engages in the housing. This results in the lips of the slit in the bottom portion being permanently pressed together, there being no possibility to relieve the lips. In order to be able, after the removal of the puncturing cannula, to push a highly flexible catheter hose through the closed lips of the radially biased bottom portion or to be able to open the lips by the weak pressure of a fluid flow, the bottom of the hollow cylinder must be very thin and yielding. In such a case, there is a danger that the slit will also open upon a weak pressure of the blood flow and that the valve will not act as a nonreturn valve. Depending on the storage time of a catheter hose, the thin lips at the biased bottom portion deform because of fatigue so that also in this valve device deformation will cause a hole that cannot be closed. In both of the known valve devices of hub members described above, the necessary additional adjusting member increases the production costs of the hub member.

It is an object of the present invention to improve a valve device of the above-mentioned type such that the slit bottom portion of the resilient hollow cylinder can be easily opened in the direction of insertion, while reliably sealing in the reflux direction.

SUMMARY OF THE INVENTION

In accordance with the present invention, this and other objectives are achieved by providing a hub member that includes a housing having a chamber open at both ends. One of the open ends of the chamber is connectable to the conduit. The opposite open end may receive a connecting member. The hub member also includes a valve having a resilient valve body in the shape of an open, cup-shaped hollow cylinder with a slit bottom portion. The hollow cylinder is axially displaceable in the chamber. A spring is provided that, in the closed position, presses the edge of the opening of the hollow cylinder against the inner end of an insertion opening for a connecting member. The insertion opening is formed in the housing and has a diameter larger than the inner circumference of the edge of the opening of the hollow cylinder. The bottom portion of the hollow cylinder extends into an adapted central hole of a closing ring fixed in the housing. The bottom portion may be pushed axially through the hole against the spring action for releasing the legs thereof formed by the slit.

The spring-loaded, axially displaceable, cup-shaped hollow cylinder of the valve device is directly actuated by a connecting member (e.g. the hub of a steel cannula or an infusion conduit) pressing on its upper edge, so that additional adjusting members are superfluous. By the displacement of the hollow cylinder against the spring action, which occurs automatically when a connecting member is inserted into the insertion opening, the bottom portion of the cylinder is pushed out of the central hole in the closing ring so that the legs of the bottom portion may spread outward freely and without stress in order to unblock the passage. Since the closing ring is inactive in the open position of the hollow cylinder and the bottom portion is then not loaded in the radial direction, a slight opening pressure will suffice. Therefore, the hub member, with a perfectly effective check valve, is suited for allowing both the passage of cannulas or catheters and the passage of liquids.

When the connecting member is withdrawn from the insertion opening the axial pressure against the hollow cylinder is thereby relieved. The spring will then immediately displace the hollow cylinder toward the insertion opening of the housing and the bottom portion will be pulled into the central hole in the closing ring. The mutual adaptation of the hole and the outer circumference of the bottom portion will lead to an enclosure of the bottom portion such that the edges of the slit in the bottom portion are kept pressed against each other without stress and so that air can not enter from outside and blood can not ooze from inside. The fact that the hollow cylinder is free from pre-stress both in the open and closed positions ensures a perfect functioning of the valve device when opened and closed repeatedly, since the material retains its inherent resilience and shows no symptoms of fatigue.

The hub member of the present invention may be provided with a dwell-in venous cannula and delivered as a puncture set ready for use with the steel cannula inserted. The hub of the steel cannula may be inserted in the insertion opening for the connecting member and may axially press against the hollow cylinder so that the bottom portion projects beyond the closing ring. The legs of the bottom portion will freely spread radially under the pressure exerted by the steel cannula, thereby opening the passage in the hollow cylinder. In this case, no internal stresses of the material occur and the edges of the legs, loosely abutting the steel cannula, are not deformed due to the fact that the bottom portion is free of load during the storage of the puncture set. The closing properties of the legs after the withdrawal of the steel cannula are optimal in both directions.

In an advantageous embodiment of the present invention it is contemplated that the hollow cylinder is of circular cross section and is surrounded by a helical spring. One end of the spring is supported on the closing ring, while the other end is fixed at the hollow cylinder. The helical spring is preferably made of metal having a suitable strength.

Advantageously, the bottom portion of the hollow cylinder is made thick and the slit in the bottom portion extends into the lateral surface of the hollow cylinder. In this way, a kind of jaw valve having two long spreadable legs is obtained with only one slit. In accordance with the present invention, the free end of the bottom portion has an outer annular cone which, in the closed position of the hollow cylinder, engages substantially fittingly with a conical recess at the proximal end of the hole in the closing ring. The two legs are consequently kept pressed together radially in the sealing position. The fact that the two legs are easily spreadable when opened does not entail disadvantageous effects in the closed position. Keeping the slit shut ensures that no blood will ooze therefrom and that no air can enter the device.

In a further embodiment of the present invention, the hollow cylinder is provided with a circular cylindrical longitudinal channel that ends in a symmetric conic recess in the inner basic surface of the bottom portion. An inner annular collar is provided at its opposite, open end. The conic recess provides a concentration, and thus an increase, of the opening force at the slit in the open position of the hollow cylinder. Since the legs formed by slitting the bottom portion have straight edges, they cannot enclose an object passed therethrough and having a circular cross section in a manner accurate to shape. Depending on the type of slits provided, at least two open triangular passages are obtained at the circumference of this elongate object, through which blood may flow. These trickling flows are held back by the inner annular collar at the distal end of the hollow cylinder. The hub member thereby meets high hygienic safety requirements for the patient and the user.

Preferably, the chamber in the housing is circular cylindrical and the closing ring is formed as a separate part from two semi-circular halves. The separation of the closing ring serves to enable the mounting of the hollow cylinder in the hub member. Preferably, the central hole in the closing ring is circular.

BRIEF DESCRIPTION OF THE DRAWINGS

A detailed description of various preferred embodiments of the invention will be made with reference to the accompanying drawings.

FIG. 4 shows a longitudinal section through a hub member of a dwell-in venous cannula in combination with a puncturing needle.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

Figure 1:
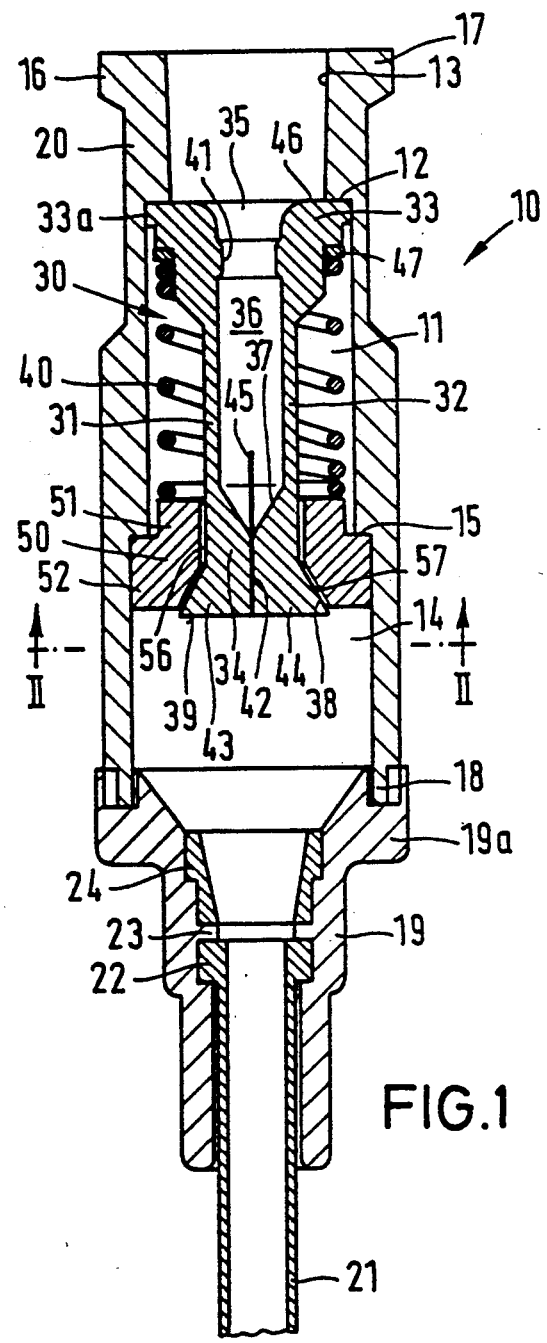
FIG. 1 shows a longitudinal section through a hub member of a catheter with a closed valve device.

As illustrated in FIG. 1, a hub member 10 includes a tubular cylindrical housing 20 of plastic material having circular inner and outer cross sections. Inside the housing 20, there is a circular cylindrical chamber 11 which, via an annular shoulder 12 at its distal end, passes into a conical insertion opening 13 for connecting members. The insertion opening 13 has a diameter smaller than that of the chamber 11.

The other end of the chamber 11 passes into a circular cylindrical space 14 via an annular shoulder 15. The diameter of the space 14 is larger than that of the chamber 11.

The distal edge of the housing 20 is provided with two diametrically opposing projections 16 and 17 that serve to lock the housing with a connecting member. Preferably, the oblique lower flanks of the projections 16 and 17 are bevelled in opposite directions with respect to the circumference.

On the proximal edge 18 of the housing 20, a hollow socket member 19 with a cap-like hub 19a is plugged and welded or glued thereto. The hollow socket member 19 is designed to connect with a flexible catheter 21 that forms a medical conduit insertable into a blood vessel or a body cavity. The catheter 21 has its rear end provided with an annular collar 22 engaging in an annular recess of the hollow socket member 19 and being secured by welding or extrusion coating. An adapter 24 with a conical passage forms a continuation of a funnel opening of the hub 19a and conveys, for example, liquid into the catheter 21.

A valve device 30 that extends into the chamber 14 is arranged in the chamber 11 of the housing 20. The valve device 30 includes an axially displaceable cup-shaped hollow cylinder 31 of resilient material with a circular cross section, a helical metal spring 40, and a closing ring 50 of rigid material.

The hollow cylinder 31 defines a circular cylindrical shaft 32 having a profiled collar 33 at one end and a bottom portion 34 at the other end. The bottom portion 34 is thick in the axial direction. The profiled collar 33 is stepped axially several times on its outer circumference. The outermost edge 33a of the collar 33 sealingly abuts the inner surface of the chamber 11. The outermost edge 33a is located in the vicinity of an opening 35 of a circular cylindrical longitudinal channel 36 of the hollow cylinder 31. The longitudinal channel 36 ends in a conical recess 37 at the inner basic surface of the thick bottom portion 34. The bottom portion 34 has a diverging outer annular cone 38 provided at its free end. The outer bottom surface 39 of the bottom portion 34 is circular and even. The longitudinal channel 36 extends over the length of the shaft 32 and, before the opening 35, it has an inner annular collar 41 that serves as a seal for an elongate object passed through the longitudinal channel 36. A longitudinal slit 42 extends into the shaft 32 and diametrically cuts the thick bottom portion 34. The slit 42 divides the bottom portion 34 into two legs 43 and 44 that may be spread apart up to the inner end 45 of the longitudinal slit 42. The inner end 45 of the longitudinal slit 42 is located near the transversal center line of the hollow cylinder 31 in the proximal half of the hollow cylinder.

The front surface 46 of the profiled collar 33 extends radially into the free cross section of the inner end of the insertion opening 13 of the housing 20 and forms a shoulder free towards the outside. A connecting member inserted into the inner cone of the insertion opening 13 will press against the front surface 46 with its edge and will displace the hollow cylinder 31.

One end of the helical spring 40 is supported on the metal disc 47 resting on the inner annular step of the profiled collar 33. The diameter of the helical spring 40 is equal over its entire length. The other end of the helical spring 40 presses against the closing ring 50. One purpose of the metal disc 47 is to prevent the helical spring 40 from pressing into the relatively softer material of the profiled collar 33. The helical spring 40 presses the hollow cylinder 31 with its front surface 46 against the annular collar 12, thereby pulling the bottom portion 34 into the closing ring 50.

Figure 2:
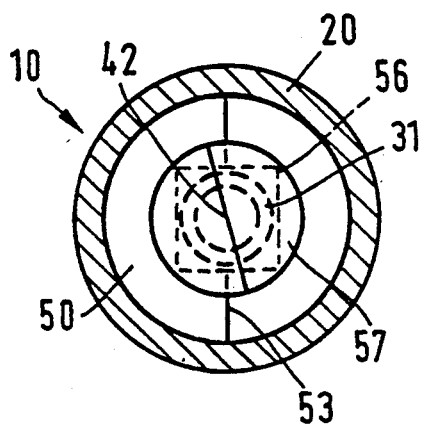
FIG. 2 shows a cross section along line II—II of FIG. 1.
Figure 3:
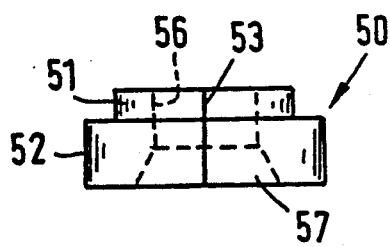
FIG. 3 shows a side view of a closing ring.

The closing ring 50 has two circular cylindrical portions 51 and 52 of different diameters that are in coaxial succession. The portion 51 forms the abutment for the spring 40, while the portion 52 sealingly fits into the enlarged chamber 14. To facilitate mounting, the closing ring 50 is diametrically divided along a line of division 53. A square or circular hole 56 is formed in the center of the closing ring 50, the sides of which abut the circular bottom portion 34 of the hollow cylinder 31 (see FIG. 2). The proximal end of the hole 56 has a diverging conical recess 57 formed therein, into which the outer annular cone 38 of the bottom portion 34 is fitted when the hollow cylinder 31 is in the closed position as shown in FIG. 1.

Figure 4:
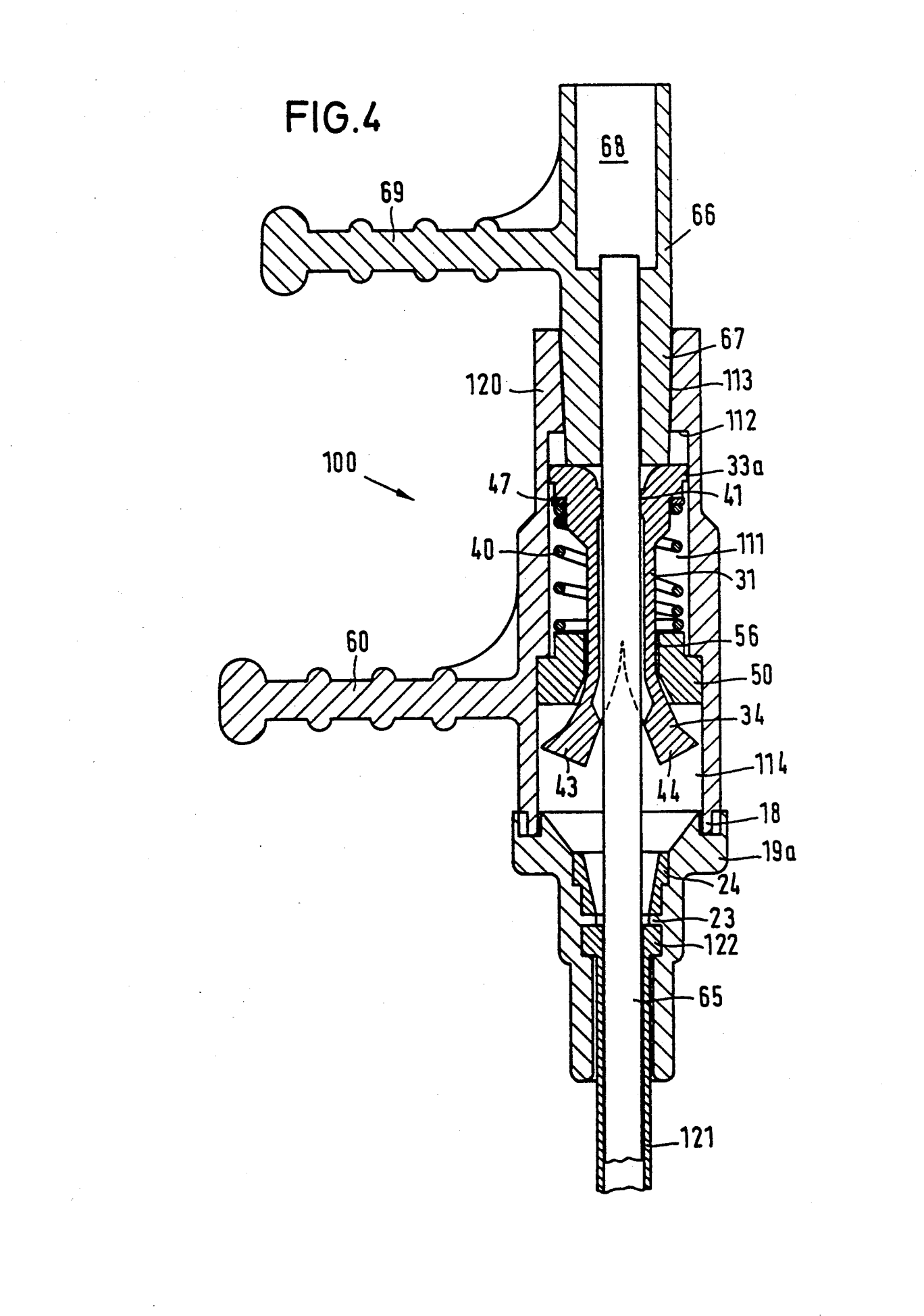
Figure 5:
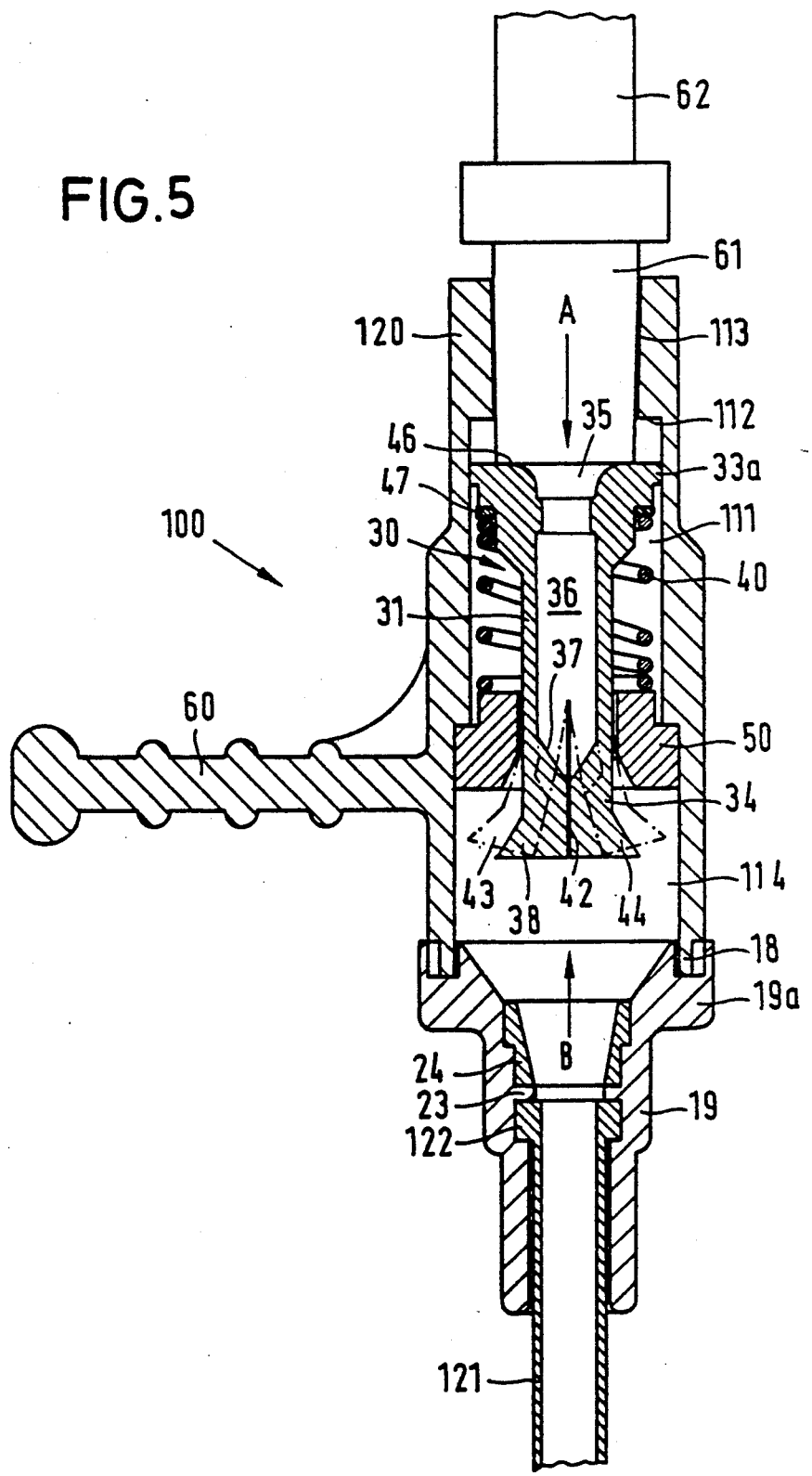
FIG. 5 shows a longitudinal section through a hub member of FIG. 4 in combination with an infusion conduit.

A hub member 100 with a valve device 30 is shown in FIGS. 4 and 5 as used in practice with a dwell-in venous cannula or an infusion conduit. In the illustrated embodiments the housing 120 (which is similar in structure to the housing 20 described above) is provided with a projecting handle plate 60 and a short dwell-in venous cannula 121 fixed at its proximal end by an annular collar 122, as described in connection with FIG. 1. The dwell-in venous cannula 121 consists of a thin-walled plastic tube providing access to a blood vessel for a short time. To this end, the blood vessel must be punctured first. This is done by means of a hollow puncturing needle 65 of steel having a sharpened point at its proximal end and being connected with a hub 66 at the opposite, distal end. The hub 66 has an outer cone 67 through which the end of the puncturing needle 65 protrudes into a cavity 68 which is open to the outside and which may be covered by a blood trapping stopper (not illustrated) for indicating a successful puncture. Further, the hub 66 has a handle plate 69 directed sideward which is parallel to the handle plate 60 of the housing 120.

As illustrated in FIG. 4, the puncturing set is assembled, aseptically packed and stored. In this state, the front edge of the outer cone 67 urges the hollow cylinder 31 away from the annular shoulder 112 of the housing 120 against the action of the helical spring 40. The two legs 43 and 44 are consequently released from the closing ring 50 and spread as shown in FIG. 4 under the pressure exerted by the puncturing needle 65. In this position, the legs 43 and 44 are not subject to any stress so that the material remains free of fatigue and the edges of the parted conical recess 37 abutting the puncturing needle 65 are not deformed.

After the puncture has been performed with the puncturing set, the puncturing needle 65 is retracted. The outer cone 67 releases the hollow cylinder 31 and the hollow cylinder is pushed back by the helical spring 40. The bottom portion 34 of the hollow cylinder 31 enters the central hole 56 of the closing ring 50. In doing so, the straight edges of the slit 42 are kept pressed together, resulting in a tight closure in both directions.

If, subsequently, the dwell-in venous cannula 121 is to be coupled with an infusion conduit, an outer cone 61 of a connecting member is inserted into the insertion opening 113, as shown in FIG. 5. The outer cone 61 of the connecting member is connected to an infusion conduit 62 leading to an infusion liquid container. The front edge of the outer cone 61 presses against the front face 46 of the hollow cylinder 31 thereby axially displacing the cylinder against the action of the spring towards the chamber 114 of the housing 120. The "bandage" for closing the bottom portion 34 of the hollow cylinder 31 that is formed by the edge of the hole 56 is thereby "slipped off", and the two legs 43 and 44 can spread radially (as indicated by the dash-dot line in FIG. 5) when a liquid flow streaming in the direction of the arrow A hits the conical recess 37 in the inner basic surface of the bottom portion 34.

Practically free of any whirling, the liquid flow may stream through the large opening between the two legs 43 and 44, keeping the same at a sufficiently large distance so that an unobstructed passage is ensured. If, for example, upon changing the infusion line 62, the outer cone 61 is pulled out of the housing 120, the helical spring 40 will immediately press the hollow cylinder 31 backward until its front face 46 abuts the annular collar 12 and the outer annular cone 38 of the bottom portion 34 is pulled into the conic recess 37 of the closing ring 50. It is the purpose of the closing ring 50 to ensure that the straight edges of the longitudinal slit 42 are held together over the entire thickness of the bottom portion 34 (FIG. 1) so that neither air can flow in from outside following the direction of arrow A, nor may blood flow out in the direction of arrow B. The longitudinally slit bottom portion 34 forms a kind of jaw valve with large-surface sealing zones between the two legs 43 and 44, due to the thickness of the bottom portion 34.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A hub member for a medical conduit, comprising:
   a housing defining a chamber having a first open end and a second open end, the first open end adapted to receive the medical conduit and the second open end defining an insertion opening adapted to receive a connecting member,
   a substantially resilient valve body axially displacable in the chamber between an opening position and a closed position, the valve body defining a hollow cylinder having a slit bottom portion including at least two substantially unbiased legs, the insertion opening defining a first diameter,
   the hollow cylinder having an inner circumferential edge defining a second diameter, the first diameter being larger than the second diameter,
   a spring for biasing the hollow cylinder toward the insertion opening,
   a closing ring fixed relative to the housing and defining an aperture, the bottom portion of the hollow cylinder being positioned to extend at least partially into the aperture of the closing ring in the closed position of the valve body,
   whereby the substantially unbiased legs of the bottom portion are held together by the closing ring in the closed position of the valve body and are released in the opening position of the valve body.

2. The hub member of claim 1 wherein the spring is substantially helical and surrounds the hollow cylinder and wherein the helical spring has a first end supported on the closing ring and a second end fixed relative to the hollow cylinder.

3. The hub member of claim 1 wherein the hollow cylinder defines a lateral surface into which the slit of the bottom portion extends, the aperture in the closing ring includes a proximal end that defines a conical recess, the bottom portion of the hollow cylinder includes a free end that defines an annular cone, and the annular cone and the conical recess are mutually configured to fittingly engage in the closed position of the valve body.

4. The hub member of claim 1 wherein the hollow cylinder defines a substantially circular cylindrical longitudinal channel having a first channel end and a second channel end, and wherein the first channel end defines a substantially symmetrical conical recess in the bottom portion and the second channel end defines an inner annular collar.

5. The hub member of claim 1 wherein the chamber is of circular cylindrical shape and the closing ring comprises two semi-circular halves.

6. A hub member for a medical conduit, comprising:
   a housing defining a chamber having a first open end and a second open end, the first open end adapted to receive the medical conduit and the second open end adapted to receive a connecting member,
   a substantially resilient valve body axially displaceable in the chamber between an opening position and a closed position, the valve body defining a hollow cylinder having a slit bottom portion including at least two substantially unbiased legs,
   a spring for biasing the hollow cylinder toward the second open end of the chamber,
   a closing ring fixed relative to the housing and defining an aperture, the bottom portion of the hollow cylinder being positioned to extend at least partially into the aperture of the closing ring in the closed position of the valve body,
   whereby the substantially unbiased legs of the bottom portion are held together by the closing ring in the closed position of the valve body and are released in the opening position of the valve body.

* * * * *